US 6,605,460 B1

(12) United States Patent
Goyal

(10) Patent No.: US 6,605,460 B1
(45) Date of Patent: Aug. 12, 2003

(54) AVIAN PNEUMOVIRUS VACCINE

(75) Inventor: Sagar M. Goyal, Roseville, MN (US)

(73) Assignee: University of Minnesota, Minneapolis, MN (US)

( * ) Notice: Subject to any disclaimer, the term of this patent is extended or adjusted under 35 U.S.C. 154(b) by 0 days.

(21) Appl. No.: 09/667,976

(22) Filed: Sep. 22, 2000

(51) Int. Cl.$^7$ .............................................. C12N 7/04
(52) U.S. Cl. .................. 435/236; 424/9.2; 424/93.1; 424/211.1; 435/235; 435/237
(58) Field of Search ................... 424/9.2, 93.1, 424/93.6, 184.1, 211.1; 435/173.3, 235.1, 236, 237, 245

(56) References Cited

U.S. PATENT DOCUMENTS

| | | | |
|---|---|---|---|
| 4,559,229 A | | 12/1985 | Page et al. |
| 5,069,902 A | * | 12/1991 | Cook et al. .................. 424/89 |
| 5,208,023 A | | 5/1993 | Nicholas et al. |
| 5,750,113 A | | 5/1998 | Cook |
| 5,846,527 A | | 12/1998 | Miller et al. |
| 6,086,892 A | | 7/2000 | Cook |

OTHER PUBLICATIONS

Sowa et al. Zur humoralen Immunenantwort beim Huhn nach Vakzinierung gegen Rhinotracheitis der Puten. Archiv fur Geflugelkunde (1999) vol. 64, pp. 55–60.*
Buys et al. The Isolation and attenuation of a virus causing rhinotracheitis in turkeys in South Africa. Onderstepoort Journal of Veterinary Research (1989) vol. 56, pp. 87–98.*
Cook J. Avian pneumovirus infections in turkeys and chickens. The Veterinary Journal (Sep. 1, 2000) vol. 160, pp. 118–125.*
Pattison M. TRT in the Field: Field situation and control. In: Proceedings & Technical Supplement of the Roche Avian Pneumovirus Workshop. ed. Clark et al. Parsoppany, NJ. (1998) RCD 9713, pp. 43–49.*
Pringle, *Arch. Virol.*, 1996, 141:2251–2256.
Roy et al., *Vaccine*, 1999, 17(20–21):2674–2676.
Shin et al., *Arch. Virol.*, 2000, 145:1239–1246.
State of MN, *Board of Animal Health Annual Report*, Jul. 1, 1998–Jun. 30, 1999.
State of MN, *Board of Animal Health Annual Report*, Jul. 1, 1999–Jun. 30, 2000.
West et al., *Vaccine*, 1999, 18(9–10):907–919.
Williams et al., *Avian Pathol.*, 1991, 20:585–596.
Prevel, "Differential of Avian Pneumovirus Isolates by Monoclonal Antibodies to Detect Turkey Rhinotracheitis Antibodies in ELISA," 1995, Tierarztliche Hochschule (pub.), Hannover, Germany (abstract only).
Ali and Reynolds, "A Reverse Transcription—Polymerase Chain Reaction Assay for the Detection of Avian Pneumovirus (Colorado Strain)," *Avian Diseases*, 1999, 43:600–603.
Gulari et al., "Protective Efficacy of High–Passage Avian Pneumovirus (APV/MN/turkey/1–a/97) in Turkeys," *Avian Diseases*, 2001, 45:593–597.
Seal, "Avian pneumoviruses and emergence of a new type in the United States of America," *Animal Health Research Reviews*, 1(1):67–72.
Alexander, *Diseases of Poultry*, 1997, pp. 541–569.
Chiang, et al., *J. Vet. Diagn. Invest.*, 2000, 12:381–384.
Cook et al., *Avian Pathology*, 1989, 18:511–521.
Cortese et al., *Am. J. Vet. Res.*, 1998, 59(11): 1409–1413.
Dar et al., *Proc. 41$^{st}$ Annual Meeting Am. Assoc. Vet. Lab. Diagn.*, 1998, pp. 15.
Dubensky et al., *Nat. Med.*, 1998, 4(12):1357–1358.
Foley et al., *J. Am. Vet. Med. Assoc.*, 1999, 214(5):620, 622.
Goyal et al., *J. Vet. Diagn. Invest.*, 2000, 12:166–168.
Hossain et al., *Vaccine*, 2000, 18(27):3082–3090.
Jones, *Avian Pathol.*, 1996, 25:639–648.
Kleven, *Proc. U.S. Animal Health Assoc. 101$^{st}$ Annual Mtg.*, 1997, pp. 486–491.
Mavromatis et al., *J. Vet. Med. B*, 1999, 16(9):603–612.
Naylor et al., *Vet. Bull.*, 1993, 63:439–449.
Pare et al., *J. Wildl. Dis.*, 1999, 35(3):430–439.
Pratelli et al., *J. Vet. Med. B*, 2000, 47(4):273–276.

\* cited by examiner

*Primary Examiner*—James Housel
*Assistant Examiner*—Ulrike Winkler
(74) *Attorney, Agent, or Firm*—Fish & Richardson P.C., P.A.

(57) ABSTRACT

Compositions and methods for ameliorating the clinical signs of an avian pneumovirus infection in a bird are disclosed. The compositions include immunologically effective amounts of an attenuated or inactivated avian pneumovirus. Methods for preparing an attenuated avian pneumovirus composition are also described.

4 Claims, 1 Drawing Sheet

AVIAN PNEUMOVIRUS VACCINE

TECHNICAL FIELD

This invention relates to avian vaccines, and more particularly to avian vaccines derived from avian pneumoviruses.

BACKGROUND

Avian pneumovirus ("APV") is a member of the Paramyxoviridae family of viruses. Pringle, *Arch. Virol.* 141:2251–2256 (1996). It is the etiological agent of turkey rhinotracheitis, causing an acute upper respiratory tract infection characterized by coughing, nasal discharge, tracheal rales, foamy conjunctivitis and sinusitis in young poults. In laying birds, there is transient drop in egg production along with mild respiratory tract illness. Jones, *Avian Pathol.*, 25:639–648 (1996). While uncomplicated cases of APV infection usually result in low mortality, secondary bacterial and/or viral infections can result in up to 25% mortality. Id.

APV was first detected in South Africa in 1978, and later diagnosed in the UK, France, Spain, Germany, Italy, Netherlands, Israel, and Asia. Alexander, *In Diseases of Poultry*; 10th edition, Barnes et al., (eds.), 541–569 (1997); and Jones, supra. The first United States APV case was in Colorado in 1996. Kleven, *Proc. U.S. Animal Health. Assoc.* 101st *Annual Mtg.*, 486–491 (1997). Subsequent APV infections were reported in Minnesota and neighboring states. Lauer, *Minnesota Poultry Testing Laboratory Monthly Report*, (1999). By 1999, at least 37% of the turkey flocks in Minnesota were positive for APV antibodies, causing economic losses of approximately 15 million dollars.

The tremendous economic pressure caused by APV outbreaks has caused some farmers to expose young turkey flocks to homogenized lungs obtained from APV infected turkeys in a desperate attempt to immunize young poults. These drastic steps taken by farmers are not safe and effective methods for protecting turkeys from APV infection. Thus, there exists a need for safe and effective vaccines against APV infections in birds including turkeys.

SUMMARY

In one aspect, the invention features a composition includes an immunologically effective amount of an attenuated avian pneumovirus. In one embodiment, the attenuated avian pneumovirus is sequestered. In some embodiments, the composition further includes an acceptable pharmaceutical carrier. In other embodiments, the attenuated avian pneumovirus is p41.

These compositions containing immunologically effective amounts of attenuated avian pneumoviruses are effective for lowering the risk of an avian pneumovirus infection in wild birds and domesticated birds. In particular, the compositions are useful for preventing an avian pneumovirus infection in poultry including turkeys, chickens, ducks, geese, pheasants, partridges, guinea fowl, peacocks. In addition, the APV compositions are effective for ameliorating of the clinical signs of an avian pneumovirus infection in a challenged bird.

In another aspect, the inventions features methods for preparing an attenuated avian pneumovirus composition by infecting or inoculating a cell culture with an avian pneumovirus, and serially propagating the infected cell culture until the avian pneumovirus becomes attenuated. In some embodiments, methods for preparing an attenuated avian pneumovirus further include the step of removing the attenuated avian pneumovirus from the infected cell culture. The cell cultures can be avian or non-avian cell cultures, or a combination thereof in any order. For example, the cell cultures can include vero cells, QT-35 cells or CEF cells. In some embodiments, the avian pneumovirus is selected from the group consisting of the European A, European B, Colorado, Minnesota 1A, Minnesota 1B, Minnesota 2A, and Minnesota 2b isolates.

In some embodiments, the infected cell culture is serially propagated at least 20 times, at least 40 times, at least 60 times, or at least 100 times, or any number of passages between 10 and 110 passages. For example, in one embodiment the infected cell culture is serially propagated 41 times.

These methods are effective for producing an attenuated avian pneumovirus that is effective for reducing or preventing the incidence of the clinical signs of an avian pneumovirus infection in poultry and, in particular, turkeys and chickens.

In another aspect, the invention features a method for preparing an attenuated avian pneumovirus composition that includes the steps of inoculating or infecting an avian cell culture with an avian pneumovirus, propagating the avian pneumovirus in the avian cell culture, inoculating or infecting a non-avian cell culture with an avian pneumovirus isolated from the propagated avian cell culture, propagating the non-avian infected cell culture until the avian pneumovirus becomes attenuated, and isolating the attenuated avian pneumovirus from the non-avian infected cell culture.

In another aspect, the invention features a method for reducing the risk of an avian pneumovirus infection in a bird by inoculating a bird with an immunologically effective amount of an attenuated avian pneumovirus composition. In some embodiments, the inoculated bird is allowed to become seropositive. Although many different dosages may be used, particularly useful dosages include inoculating a bird with at least $1.6 \times 10^6$ TCID$_{50}$ of the attenuated avian pneumovirus composition, at least $1 \times 10^2$ TCID$_{50}$ of the attenuated avian pneumovirus composition, or at least $1 \times 10^1$ TCID$_{50}$ of the attenuated avian pneumovirus composition.

Any method of inoculation can be used including applying the composition to one or more eyes of a bird and/or one or more nostril of a bird, or perhaps supplying the attenuated avian pneumovirus composition in the drinking water of a bird. Inoculated birds can be members of a flock of birds and the inoculated or vaccinated birds can cause a majority of the flock to become seropositive. In some embodiments, the method is effective for reducing the incidence of the clinical signs of an avian pneumovirus infection in a challenged bird.

In another aspect, the invention features, an inoculated bird, which is a bird containing an inoculant of an immunologically effective amount of an isolated attenuated avian pneumovirus. In some embodiments, the bird is allowed to become or is seropositive for avian pneumovirus. In another aspect, the invention features a body part, such as a meat portion, of an inoculated or vaccinated bird. In particular, these birds can be turkeys.

In yet a further aspect, the invention features compositions containing immunologically effective amounts of inactivated avian pneumovirus. In some embodiments, the composition further includes an acceptable pharmaceutical carrier or adjuvant. In other embodiments, the inactivated avian pneumovirus is an inactivated form of an attenuated avian pneumovirus such as an inactivated form of p41. Compositions containing inactivated avian pneumoviruses are also effective for lowering the risk of an avian pneumovirus infection in poultry, such as chickens or turkeys, and in other domesticated and wild birds. The composition are also effective for ameliorating the clinical signs of an avian pneumovirus infection in a challenged bird. In some embodiments, the avian pneumovirus is a formalin or β-propiolactone inactivated avian pneumovirus.

In another embodiment, the invention features a composition containing an immunologically effective amount of an isolated attenuated avian pneumovirus wherein the attenuated avian pneumovirus became attenuated by propagating an avian pneumovirus in a non-avian host, such as a vero cell. In other embodiments, the composition containing an immunologically effective amount of an isolated attenuated avian pneumovirus was serially propagated in an avian host before being propagated in a non-avian host in vitro.

In another embodiment, a method for preparing an attenuated avian pneumovirus composition includes the steps of infecting a host with an avian pneumovirus, propagating the avian pneumovirus in the host, infecting a cell culture with an avian pneumovirus isolated from the propagated host, propagating the infected cell culture until the avian pneumovirus becomes attenuated, and perhaps isolating the attenuated avian pneumovirus from the non-avian infected cell culture. Useful hosts for such a method include embryonated chicken eggs, embryonated turkey eggs, and tracheal organ cultures. Useful cell cultures for such a method include chicken embryo fibroblast, quail tumor cell lines, and vero cells.

In another aspect, the invention features an article of manufacture containing attenuated or inactivated APV compositions. The compositions can be combined with packaging materials and instructions for their use. The articles of manufacture may combine one or more isolated attenuated or inactivated APV vaccines. In addition, the articles of manufacture may further include antibodies, indicator molecules, and/or other useful agents for detecting other avian diseases together with isolated attenuated APV vaccines. The instructions can describe how an isolated attenuated or inactivated APV vaccine is effective for preventing the incidence of an APV infection, preventing the occurrence of the clinical signs of an APV infection, ameliorating the clinical signs of an APV infection, lowering the risk of the clinical signs of an APV infection, lowering the occurrence of the clinical signs of an APV infection and/or spread of APV infections in birds.

Articles of manufacture can also include diagnostic molecules that are effective for detecting the presence of APV or other avian infections in birds. Moreover, it is to be understood that isolated attenuated or inactivated APV vaccines themselves and/or articles of manufacture that include isolated attenuated or inactivated APV vaccines can include other components conventional to the art, for example sterile water, pharmaceutical carriers, vaccine carriers, and buffers that are useful for maintaining the viability of the APV vaccines. The APV vaccines and/or articles of manufacture may also contain other attenuated or inactivated virus strains, microorganisms, and antigens that protect the inoculated birds against other avian diseases. Conveniently the isolated attenuated APV vaccines may be provided in a pre-packaged form in quantities sufficient for a protective dose for a single bird or for a pre-specified number of birds in, for example, sealed ampoules, capsules or cartridges.

It is to further understood that each of the embodiments may be combined with any of the other embodiments described herein. For example, the methods disclosed herein are useful with any of the compositions, or articles of manufacture, and the dosages may be used in any of the various embodiments described herein.

Advantages of the invention include a safe and effective way to protect birds, especially turkeys, from an APV infection. Moreover, the invention can provide methods for raising antibodies to APV to be used in diagnostic kits and may be used in the diagnostic kits for detecting the presence of APV.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. Amino acid designations may include full name, three letter, or single letter designations as commonly understood by one of ordinary skill in the art to which this invention belongs. In case of conflict, the present specification, including definitions, will control. In addition, the materials, methods, and examples are illustrative only and not intended to be limiting.

The details of one or more embodiments of the invention are set forth in the accompanying drawings and the description below. Other features and advantages of the invention will be apparent from the following detailed description, and from the claims.

DESCRIPTION OF DRAWINGS

Like reference symbols in the various drawings indicate like elements.

DETAILED DESCRIPTION

Figure 1:
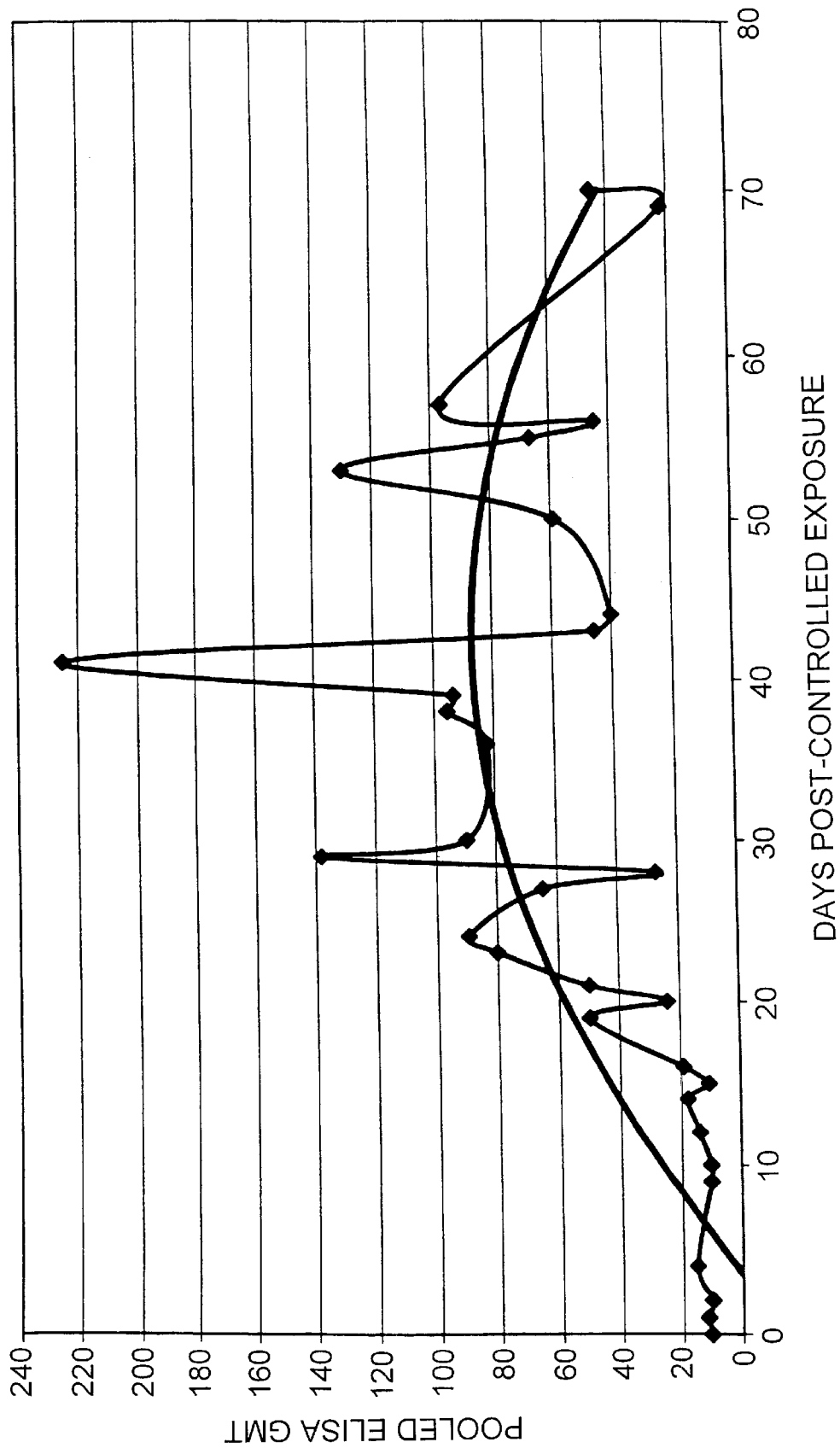
FIG. 1 is a graphical representation of Table 1 plotting the geometric mean titer for measuring seroconversion of turkeys inoculated with a 41 passage attenuated APV vaccine.

The invention features methods, compositions of matter, and articles of manufacture (kits) containing an avian composition or vaccine that is derived from an avian pneumovirus ("APV"). An avian composition or vaccine can contain an immunologically effective dosage of an attenuated APV. Such a vaccine can be produced by serially propagating a virulent form of APV in a cell culture until the APV becomes attenuated. These APV vaccines are both safe and immunogenic when administered to birds. Vaccinated birds are seropositive for anti-APV antibodies and resistant to infection by or challenge with a virulent APV. Using the compositions and/or vaccines described herein is an effective way for preventing, ameliorating, lowering the risk of, lowering the occurrence of and/or spread of APV infections in birds. An avian composition or vaccine can contain an immunologically effective dosage of an inactivated APV.

Compositions Containing Attenuated Vaccines and Their Use

As used herein, live vaccines are synonymous with attenuated vaccines. Attenuated APV vaccines are compositions containing a sufficiently attenuated avian pneumovirus and these vaccines are useful for any type of bird susceptible to APV infection including domesticated and wild birds. In particular, the vaccines described herein are useful for inoculating and/or treating birds living in flocks or other types of close living arrangements where an APV infection can rapidly spread from bird to bird. Domesticated birds that may benefit from receiving an APV vaccine include poultry such as turkeys, chickens, ducks, geese, pheasants, partridges, guinea fowl, peacocks, and any other type of domesticated bird. Wild birds that may benefit from receiving an APV vaccine include starlings, sparrows, turkeys, ducks, geese, pheasants, partridges, guinea fowl, peacocks, and any other type of wild bird that may contract an APV infection and/or transmit APV infection to a domesticated bird.

An immunologically effective dosage of an attenuated APV vaccine is a dosage that, when administered to a bird, elicits an immunological response in the bird but does not cause the bird to develop severe clinical signs of an APV infection. A bird that has received an immunologically effective dosage is an inoculated bird or a bird containing an inoculant of an immunologically effective amount of an isolated attenuated avian pneumovirus. When the bird elicits an immunological response it is considered seropositive, i.e., produces a detectable amount of anti-APV antibodies. Methods for detecting an immunological response in a bird are known, e.g., Chiang et al., "A Modified Enzyme-linked Immunosorbent Assay for the Detection of Avian Pneumovirus Antibodies," *J. Vet. Diag. Invest.*, 12:381–84 (2000). A vaccinated bird is an inoculated bird that is seropositive. A vaccinated bird may shed the attenuated APV. APV shedding is typically detectable from about 5 days to about 7 days post inoculation, and may range from 3 days to 21 days post inoculation. Methods for detecting the shedding of an APV are known. Useful methods include the methods described in Shin et al., "Specific Detection of Avian Pneumovirus (APV) US Isolates by RT-PCR," *Arch. Virol.*, 145:1239–46 (2000); Goyal et al., "Isolation of Avian Pneumovirus from an Outbreak of Respiratory Illness in Minnesota Turkeys," *J. Vet. Diagn. Invest.*, 12:166–68 (2000).

Vaccinated birds elicit an immunological response to a challenge with a virulent APV. Vaccinated birds can be resistant to or immune to a subsequent APV infection when challenged with a virulent form of APV. As a result, vaccinated birds that are subsequently challenged with a virulent APV may still pass slaughter inspections and continue to market. Methods and rating systems for passing or condemning birds destined for slaughter are known.

Virulent APV forms or isolates are those APV forms that cause a bird, which has not been exposed to APV and/or an APV vaccine, to develop severe clinical signs of an APV infection, to be unfit for market, and/or die. An APV form is virulent if it causes severe clinical signs of an APV infection in a bird at a dosage of at least $1 \times 10^2$ tissue culture infective dose ($TCID_{50}$).

Methods for computing virus titers are known. Any method for computing virus titers may be used. The $TCID_{50}$ is the reciprocal of the highest dilution of a virus that causes a specified reaction in 50% of the material inoculated with, or exposed to, that dilution of virus. It is common to express virus titers as $TCID_{50}$ when cell cultures are used as the indicator system. In such cases $TCID_{50}$ is the dilution that causes 50% of the cell cultures to elicit the specified reaction(s) and/or cytopathic effects, such as cell rounding. See, e.g., Cook et al., "A Live Attenuated Turkey Rhinotracheitis Virus Vaccine. 1. Stability of the Attenuated Strain," *Avian Pathology*, 18:511–522 (1989).

A vaccinated bird is resistant to or immune to an APV infection if it fails to develop severe clinical signs of APV infection after being challenged with a virulent APV. A resistant or immune bird may develop no clinical signs or mild clinical signs of an APV infection when exposed to a virulent APV. The clinical signs of APV and other upper respiratory infections in birds are known. The clinical signs of an APV infection in turkeys include profuse ocular and nasal discharge, watery eyes, unilateral or bilateral sinus swelling, facial edema or swelling, depression, coughing, sinusitis, airsacculitis, respiratory distress, and mortality. In laying turkeys, a drop in egg production associated with respiratory distress may be seen.

Immunologically effective dosages can be determined experimentally and may vary according to the type, size, age, and health of the bird vaccinated. For example, an effective amount for a two-week-old turkey poult may include an APV vaccine dosage of about 200 µl of a $1.6 \times 10^6$ $TCID_{50}$/ml stock vaccine solution. It is preferable to give a dosage of at least about $1 \times 10^2$ $TCID_{50}$/bird. Dosages smaller than $1 \times 10^2$ $TCID_{50}$/bird may result in ineffective vaccinations, and larger dosages may be less cost effective. Older turkeys may require larger dosages. The vaccination may include a single inoculation or multiple inoculations. Other dosage schedules and amounts including vaccine booster dosages may be useful.

The age of the bird receiving a vaccination may depend upon the type of bird and the purpose for which the bird is being kept. For example it may be preferable to inoculate meat-producing birds at a young age, perhaps as new borns or hatchlings or when the birds are only a few weeks old. Alternatively, it may be useful to vaccinate egg-producing birds at other times, e.g., shortly before they are about to lay (perhaps with a vaccine booster dosage) so that maternal antibodies may be transmitted to the young. Of course, it may also be useful to inoculate egg-laying birds at an early age to prevent APV infection in the egg-laying flock.

The immunologically effective dosage may be given to a bird using any known method for inoculating birds with attenuated vaccines including direct application intranasally, intraocularly, and/or as a subcutaneous or intramuscular injection. The inoculation can be given to a single nostril or eye or divided between one or more nostril or eye. For example, a 200 µl dosage containing $1.6 \times 10^6$ $TCID_{50}$/ml can be evenly divided into four 50 µl dosages for both nostrils and eyes. The immunologically effective dosage may be given to a representative sample or subset of a flock. For example, at least 2 poults/1000 poults may be directly inoculated. Other bird samples including at least 1 bird/1000 birds, at least 5 birds/1000 birds, and at least 100 birds/1000 birds may be directly inoculated. The directly inoculated birds are then allowed to commingle with the rest of the flock and passively inoculate the other members of the flock. One way that the directly inoculated birds may inoculate other birds is through shedding of the attenuated APV vaccine. Directly inoculating a subset of the flock creates a rolling or sequential vaccination as the attenuated vaccine is passed from bird to bird. The number of vaccinated birds in the flock increases as the directly vaccinated birds interact with the rest of the flock. In the end, a majority or all of the birds should become vaccinated.

Alternatively, an immunologically effective dosage may be given to each member of a flock directly or the dosage can be applied to the food and/or water supply of a flock. For example, an immunologically effective dosage, e.g., about $10^3$ $TCID_{50}$/bird, can be dissolved in the water supply of a flock of birds. Most, if not all, of a flock should become vaccinated birds at approximately the same time when inoculating the flock through the food or water supply. Dosages administered through the food or water supply can be easily computed by multiplying the amount a single bird eats or drinks per day by the number of birds to be inoculated to compute the unit of food or water consumed per day per bird. Then, the unit of food or water consumed per day is used to compute the vaccine dosage needed to dissolve in that unit of food or water so as to deliver at least $10^2$ TCID$_{50}$/bird.

APV compositions or vaccines containing an inactivated APV can be used in the same manner and under the same conditions used for attenuated APV compositions. Inactivated APV vaccines are compositions containing an inactivated avian pneumovirus and these vaccines are useful for any type of bird susceptible to APV infection including domesticated and wild birds. Methods for making inactivated virus vaccines are well known and include the use of formalin or β-propiolactone to make inactivated vaccines. Virulent and attenuated APV particles may be converted to inactivated forms using formalin or β-propiolactone. Inactivated APV compositions or vaccines are typically administered by subcutaneous or intramuscular injection because they are no longer living. Such compositions may further include an adjuvant and/or pharmaceutical carrier.

Compositions containing an attenuated or inactivated APV also have uses other than as a vaccine. These compositions may be used to induce a bird to raise antibodies to APV to be used in diagnostic tests for identifying one or more APV isolates. Further the attenuated APV may be used in a diagnostic assay for detecting the presence of anti-APV antibodies in the sera of a bird. Methods for raising and purifying antibodies are known. Methods for preparing diagnostic kits for detecting antibodies in a serum source are known.

Methods for Making Attenuated Vaccines

Any APV form or isolate can be used to prepare an attenuated APV vaccine. It may be preferable to use a virulent form of an APV. Suitable virulent APV isolates for preparing turkey vaccines include the European A, European B; Colorado, Minnesota 1A, Minnesota 1B, Minnesota 2A, Minnesota 2b, and any other isolates that are identified in the future.

Attenuated APV vaccines may be combined with different vaccines or preventative methods directed to other avian diseases so as to produce birds that are relatively pathogen free, healthier, and/or resistant to more avian diseases than just APV. Other avian diseases include *Ornithobacterium rhinotracheale, Bordetella avium, avian influenza, New Castle Disease*, Mycoplasma spp., and *Pasteurella multocida.*

An attenuated APV vaccine can be produced by first isolating an APV, attenuating the APV, and finally isolating an attenuated APV vaccine. The APV attenuated vaccines described herein can be produced using any known method for producing attenuated vaccines. See e.g., Williams et al., "Further Studies on the Development of a Live Attenuated Vaccine against Turkey Rhinoiracheitis," *Avian Pathology*, 20:585096 (1991). An illustrative method for producing an attenuated APV vaccine is presented below.

APV can be isolated using any known method for isolating avian viruses. The methods described in Goyal et al., "Isolation of Avian Pneumovirus from an Outbreak of Respiratory Illness in Minnesota Turkeys," *J. Vet. Diagn. Invest.*, 12:166–68 (2000) provide illustrative methods for isolating a turkey APV. The methods described in Goyal et al. may be adapted for other avian viruses. Known methods for isolating APV can include the step of obtaining inoculation specimens from birds, such as turkeys, that are exhibiting the clinical signs of an APV infection. Specimens can be obtained using tracheal swabs, turbinates, or by isolating the trachea and/or lungs. The inoculation specimens are then used to inoculate hosts such as embryonated chicken eggs ("ECE"), embryonated turkey eggs ("ETE") or tracheal organ cultures ("TOC").

Subsequently, the APV virus can be adapted to other cell culture hosts such as chicken embryo fibroblasts ("CEF"), quail tumor cell lines or vero cells using known methods. See Naylor et al., "Turkey Rhinotracheitis: a Review," *Vet. Bull.*, 63:439–49 (1993). Useful quail tumor cell lines include QT-35. Useful vero cells include those available from the American Type Culture Collection ("ATCC") having the designation CCL81. The inoculated cell culture hosts are incubated and serially passaged under standard conditions. It may be necessary for the inoculated cell culture hosts to undergo one or more blind passages before cytopathic effects, such as cell rounding, are observed. Cytopathic effects for various cell cultures are well known. Cell cultures may be inoculated at each passage using any known method. Typically, cell cultures are subjected to repeated freezing and thawing to release the APV. Cellular debris is removed by centrifugation and the supernatant is then used to inoculate the next cell culture. Although the length of each passage may vary, each passage is typically 4–5 days in length. Identification of the passaged virus can be confirmed using any known method including RT-PCR. The presence of APV in the cell cultures during isolation can be confirmed using RT-PCR as described in Dar et al., "PCR-based Detection of a Newly Emerging Avian Pneumovirus," *Proc. Annual Meeting Am. Assoc. Vet. Lab. Diagn.*, 41:18 (1998).

Alternatively, APV may be directly isolated from an inoculation specimen using CEF, quail tumor cells, or vero cells. Briefly, tracheal swabs are used to inoculate monolayers of CEF, quail tumor cells, or vero cells. The cell cultures are serially passaged until cytopathic effects are observed. APV particles are then isolated by freezing and thawing the cell cultures. The experimental conditions and techniques used for serially passaging and isolating APV are known. Again, the presence of APV in the cell cultures during isolation can be confirmed using RT-PCR.

An isolated APV may be attenuated by serially passaging the APV in a suitable cell line. Useful cell lines include CEF, quail tumor cells, and vero cells. The number of passages needed to adequately attenuate APV may vary according to the APV strain and the type of cell culture used. As a virus becomes adapted to a cell line the length of each passage may shorten. Accordingly, it may be necessary to test a putative vaccine at different passage levels so as to identify a properly attenuated APV. An APV is sufficiently attenuated when a dosage of about $10^2$ $TCID_{50}$ causes no clinical signs or mild clinical signs of APV infection in a test bird. Mild clinical signs may include watery eyes, nasal discharge or cough in a flock from about 5 to about 12 days post inoculation ("dpi"). Continued passaging may further attenuate the APV. It may be necessary to serially passage the APV at least 10, 20, 30, 40, 50, 60, 70, 80, 90, 100, or more times to adequately attenuate the APV. Passaging the APV virus in cell culture can cause the virus to adapt to the cell culture causing it to become less virulent to its original host.

The attenuated APV can be sequestered from cell culture using any known method for removing a virus from cell culture. Useful methods include repeated freezing and thawing, or sonication, of a cell culture used to passage the virus. An attenuated APV is sequestered when it has been removed from its original host, serially passaged in cell culture a sufficient number times, and removed from cell culture so that administering a dosage of at least $10^2$ TCID$_{50}$ of the attenuated APV to a bird that has not been exposed to APV produces no clinical signs or mild clinical signs of an APV infection in the bird. An attenuated APV is considered removed if it is in a form that can be administered to a bird.

It may also be useful to isolate, identify, serially passage, and titrate an APV in a single cell type. For example, an APV vaccine may be developed using only CEF cells, only QT-35 cells, or only vero cells. Furthermore, it may be useful to develop attenuated APV vaccines to a variety of known APV isolates. Known APV isolates include European A, European B, Colorado, Minnesota 1A, Minnesota 1B, and Minnesota 2A isolates. Varying the APV isolate may enhance the immunogenic response in the vaccinated birds.

A useful attenuated APV composition includes APV vaccine p41. Vaccine p41 was deposited with the ATCC on Sep. 19, 2000 and received ATCC No. PTA-2483. APV vaccine p41 was serially passaged multiple times in CEF cells followed by multiple serial passages in vero cells for a total of 41 passages. These 41 passages caused the virus to adapt to the vero cell culture causing it to become less virulent to its original host, in this case, turkeys. APV vaccine p41 is an attenuated vaccine that is safe and immunogenic in turkeys.

Another useful attenuated APV composition includes APV vaccine p63. Vaccine p63 was deposited with the ATCC on Nov. 30, 2000 and received ATCC No. PTA-2752. APV vaccine p63 was generated by serially passaging p41 multiple times in vero cells for a total of 63 passages. These 63 passages caused the virus to adapt to the vero cell culture causing it to become less virulent to its original host, in this case, turkeys. APV vaccine p63 is an attenuated vaccine that is safe and immunogenic in turkeys.

Article of Manufacture Containing Isolated APV Polypeptides

Attenuated or inactivated APV compositions or vaccines as described herein can be combined with packaging materials including instructions for their use to be sold as articles of manufacture or kits. Components and methods for producing articles of manufactures are well known. The articles of manufacture may combine one or more isolated attenuated APV vaccines as described herein. In addition, the articles of manufacture may further include antibodies, indicator molecules, and/or useful agents for detecting other avian diseases together with isolated attenuated APV vaccines. Instructions describing how an isolated attenuated or inactivated APV vaccine is effective for preventing the incidence of an APV infection, preventing the occurrence of the clinical signs of an APV infection, ameliorating the clinical signs of an APV infection, lowering the risk of the clinical signs of an APV infection, lowering the occurrence of the clinical signs of an APV infection and/or spread of APV infections in birds may be included in such kits. The article of manufacture can also include diagnostic molecules that are effective for detecting the presence of APV or other avian infections in birds.

It is to be understood that isolated attenuated or inactivated APV vaccines themselves and/or articles of manufacture that include isolated attenuated or inactivated APV vaccines can include other components conventional to the art, for example sterile water, pharmaceutical carriers, vaccine carriers, and buffers that are useful for maintaining the viability of the APV vaccines. The APV vaccines and/or articles of manufacture may also contain other attenuated or inactivated virus strains, microorganisms, and antigens that protect the inoculated birds against other avian diseases. Methods for producing such multi-effect vaccines are known. Conveniently the isolated attenuated APV vaccines may be provided in a pre-packaged form in quantities sufficient for a protective dose for a single bird or for a pre-specified number of birds in, for example, sealed ampoules, capsules or cartridges.

The invention will be further described in the following examples, which do not limit the scope of the invention described in the claims.

EXAMPLE 1

Creating an Attenuated APV Vaccine

An APV isolate was identified according to the methods of Goyal et al., "Isolation of Avian Pneumovirus from an Outbreak of Respiratory Illness in Minnesota Turkeys," *J. Vet. Diagn. Invest.*, 12:166–68 (2000).

Briefly, tracheal swabs and turbinate samples taken from turkeys that were positive for APV by RT-PCR were frozen at −20° C. The trachea and turbinate samples were homogenized in 5 volumes of Hank's balanced salt solution containing an antibiotic mixture (50 U/ml penicillin, 50 µg/ml streptomycin, 50µg/ml neomycin, 1µg/ml fungizone). Suspensions were then suspended in veal infusion broth (available from Difco Laboratories, Detroit, Mich.) that contained the antibiotic mixture. After centrifugation at 2,000× g for 10 minutes, the supernatants were decanted and used for virus isolation. Cell cultures used were CEF, Vero cells, and QT-35 cells. All samples were inoculated in monolayers of CEF and QT-35 cells. The cell culture medium was decanted, and a suitable amount of sample was added to cover the entire monolayer. The inoculated cultures were incubated at 37° C. in a humid chamber for 2 hours. After virus absorption, the fluid was removed, and minimal essential medium containing 4% fetal bovine serum, 0.1 mM amino acids, 0.1 mM sodium pyruvate, 5 mg/ml lactalbumin hydrolysate, 15 mM HEPES buffer, and the antibiotic mixture were added. The inoculated cell cultures were incubated at 37° C. in a humid atmosphere with 5% $CO_2$ and were examined daily for the appearance of cytopathic effects. For blind passages, the inoculated cell cultures from the previous passage were frozen and thawed twice after 6–8 days of incubation, and the mixture of cells and medium was inoculated in fresh monolayers of cells in the same manner as described above. Samples were examined by RT-PCR to confirm the presence of APV. Cytopathic effects were first seen after at least 2 blind passages and cytopathic effects were seen in CEF cells from between 5 passages and 7 passages. The cytopathic effects were cell rounding, clumping and the formation of syncytia. The APV isolates were then adapted to Vero cells. The cytopathic effects observed for the vero cells was similar to the effects observed for the CEF cells. Negative contrast microscopy revealed pleomorphic particles that were roughly spherical, 130–200 nm in diameter with spaced surface projections of about 13 nm.

As described above, an APV isolate was serially propagated multiple times in CEF cells. The APV isolate was then removed from the CEF cell culture by repeated freezing and thawing of the CEF cell culture. A monolayer of vero cells, ATCC No. CCL81, was inoculated with the APV isolate that was removed from the CEF cell culture. The APV isolate was then serially passaged multiple times in vero cells. The attenuated APV composition was isolated from the vero cell culture and titrated using serial ten-fold dilutions according to conventional techniques. The attenuated APV composition had a concentration or titer of $5\times10^6$ TCID$_{50}$/ml and was named p41.

EXAMPLE 2

Determining the Safety and Efficacy of p41 under Field Conditions of Controlled Exposure The p41 composition of Example 1 was used to inoculate 10 separate flocks of 2-week-old turkey poults on two different farms (6 flocks on Farm A and 4 flocks on Farm B). Flock size ranged from about 20,000 to about 49,000 birds. 2 poults per 1000 birds were inoculated with approximately 200 µl of p41 (50 µl per eye and 50 µl per nostril) for 9 of the 10 flocks. The tenth flock was inoculated by dissolving $10^3$ TCID$_{50}$/bird in the drinking water of a 20,000 bird flock.

Transmission of p41 from directly inoculated birds to in-contact birds (passively inoculated) was determined by using RT-PCR virus detection and serology.

Choanal swabs from a sample of in-contact birds were tested by RT-PCR according to the method of Shin et al., "Specific Detection of Avian Pneumovirus (APV) US Isolates by RTPCR," *Arch. Virol*., 145:1239–46 (2000). The PCR tests revealed that in-contact birds were shedding p41 as early as 6 dpi. The flock inoculated through the drinking water was shedding p41 at about 5 dpi.

Serum samples from 15 birds for each flock were collected randomly at weekly intervals from the 10 flocks at farms A and B. These sera were tested for anti-APV antibodies using the method of Chiang et al., "A Modified Enzyme-linked Immunosorbent Assay for the Detection of Avian Pneumovirus Antibodies," *J. Vet. Diag. Invest*., 12:381–84 (2000). The geometric mean titer ("GMT") of anti-APV antibodies before p41 exposure was 10 (no antibody for APV) and started to rise after 15 dpi for the directly inoculated flocks. All birds of flocks 1–9 were seropositive (GMT >20) within 3 weeks post p41 exposure. Peak antibody titers were observed at 40 dpi and consistently high titers were maintained for up to 10 weeks post-exposure. All birds in the $10^{th}$ flock (drinking water inoculated) were seropositive (GMT≅38) at 14 dpi. The results are shown in Table 1 and FIG. 1. The water inoculation resulted in earlier seroconversion dpi but the overall pattern of seroconversion was similar in either mode of inoculation.

Clinical signs of APV in the p41 inoculated birds were mild and consisted of watery or cough in some flocks at 12 dpi.

Vaccination with p41 decreased the average mortality at Farm A from 9.8% in 1999 to 7.0% in 2000 when p41 was used. Average condemnation rates by slaughter inspectors also decreased slightly but medication costs increased. Farm B had a concomitant decrease in condemnation, medication, and mortality rates. See Table 2.

TABLE 2

Effect of Attenuated APV Controlled Exposure on Medication Costs, Condemnation Rates, and Mortality Rates

| Farm | Medication cost/head | % Condemnation | % Mortality |
|---|---|---|---|
| A | 0.04 (0.01) | 1.1 (1.8) | 7.03 (9.82) |
| B | 0.04 (0.17) | 2.6 (4.7) | 0.8 (7.0) |

*Figures in parenthesis represent corresponding values from the same farms for 1999 without attenuated APV controlled exposure.

EXAMPLE 4

Resistance to Virulent APV Infection

A subset of the birds identified in Example 2 were transferred to the poultry isolation building at the University of Minnesota. Birds were challenged with virulent APV at different ages as set forth in Table 3. The titer of the virulent APV was $5\times10^6$ $TCID_{50}$/ml. Each bird received a 200 $\mu$l inoculation (50 $\mu$l per eye and nostril).

Control birds (no exposure to attenuated APV) of similar ages were also challenged with virulent APV. No clinical signs of APV were observed in p41 inoculated birds on challenge at 2, 6, and 10 weeks post-virulent APV challenge.

TABLE 1

ELISA GMT ALL FARMS AT DIFFERENT AGE POST-EXPOSURE

| | AGE POST-EXPOSURE (WEEKS) | | | | | | | | | | | | | |
|---|---|---|---|---|---|---|---|---|---|---|---|---|---|---|
| FARM | 0 | 1 | 2 | 3 | 4 | 5 | 6 | 7 | 8 | 9 | 10 | 11 | 12 | 13 |
| 1 | 25 | — | — | — | 54 | 79 | 110 | 59 | 96 | — | — | — | — | — |
| 2 | 10 | — | — | 54 | — | 54 | — | — | — | — | — | — | — | — |
| 3 | 22 | — | 10 | — | 33 | 80 | 81 | — | 225 | 45 | 45 | — | — | — |
| 4 | 10 | — | — | — | 38 | — | 65 | — | — | — | — | — | — | — |
| 5 | 10 | — | 10 | — | 47 | — | — | — | — | — | — | — | — | — |
| 6 | 10 | — | — | 30 | — | 173 | — | — | — | — | — | — | — | — |
| 7 | 10 | 10 | — | 130 | — | — | — | — | 130 | — | 520 | 422 | 520 | 394 |
| 8 | 11 | 11 | — | — | 95 | — | — | — | — | — | — | — | 625 | 128 |
| 9 | 11.5 | 10.5 | — | — | — | — | 93.5 | — | — | — | 503 | — | 378 | — |
| 10 | — | — | 37 | 50 | 320 | — | 40 | — | 14 | — | — | — | — | — |

1. Norling Silo, 2. Milcreek, 3. Norling Crown, 4. Hanson, 5. Agar-Hilltop, 6. Bartel-Quam + Swam Lake, 7. Trudy Brooders/3, 8. Brian Brooders/4, 9. Dans & Trudys/5, 10. Dans Brooders/7
"—" = not measured

EXAMPLE 3

Mortality and Economic Impact of p41 Controlled Exposure

Safety and efficacy of controlled exposure with the p41 composition was determined by documenting mortality, condemnation rates, and medication costs for the flocks identified in Example 2. These data were compared with economic data from the same farms from the year before.

Control birds of 4 and 8 weeks of age exhibited clinical signs of APV infection including sinusitis, watery eyes, and nasal discharge at 3–8 dpi. The clinical signs of APV infection were scored according to a slightly modified method of Cook et al., "A Live Attenuated Turkey Rhinotracheitis Virus Vaccine. 1. Stability of the Attenuated Strain," *Avian Pathology*, 18:511–522 (1989). The clinical scores assigned to various clinical signs exemplified in Cook et al. were modified as shown in Table 4.

TABLE 3

Experimental Virulent APV Challenge in Attenuated APV Controlled Exposure Birds

| Inoculated with Vaccine | Age (weeks) | No. of Birds | Avg. Clinical Score | RT-PCR Detection of APV | | GMT | | |
|---|---|---|---|---|---|---|---|---|
| | | | | 4 days | 7 days | 0 days | 12 days | 19 days |
| + | 4 | 4 | 8 | − | − | 17 | 61 | 70 |
| + | 8 | 5 | 0 | − | − | 40 | 538 | 381 |
| + | 18–23 | 8 | 0 | − | − | 90 | 570 | 143 |
| − | 4 | 7 | 89 | + | + | 0 | 17 | 30 |
| − | 8 | 15 | 22 | + | − | 0 | 10 | 11 |
| − | 14 | 10 | 35 | − | − | 0 | 22 | 15 |

"−" = No APV detected by RT-PCR; "+" APV detected by RT-PCR.

TABLE 4

Clinical Scoring for Signs of Experimental APV Infection

| | Clinical Score for | |
|---|---|---|
| | Unilateral | Bilateral |
| Nasal Discharge | 1 | 2 |
| Watery Eye | 2 | 3 |
| Moderate Sinus Swelling | 4 | 5 |
| Severe Sinus Swelling | 5 | 6 |

Control and vaccinated birds at 4 and 8 weeks of age shed virulent APV at about 5 days post challenge and 4 week old birds also shed virulent APV at 8 days post challenge. Vaccinated birds had significantly lower scores for signs of APV infection.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising an immunologically effective amount of an attenuated avian pneumovirus, wherein said attenuated avian pneumovirus is designated passage 41 (p41) and is assigned ATCC Accession No. PTA-2483.

2. An attenuated virus, wherein said virus results from further passage of the attenuated avian pneumovirus of the composition of claim 1.

3. A composition comprising an immunologically effective amount of an attenuated avian pneumovirus, wherein said attenuated avian pneumovirus is designated passage 63 (p63) and is assigned ATCC Accession No. PTA-2752.

4. An attenuated virus, wherein said virus results from further passage of the attenuated avian pneumovirus of the composition of claim 3.

* * * * *